(12) United States Patent
Kunzler

(10) Patent No.: US 7,294,131 B2
(45) Date of Patent: Nov. 13, 2007

(54) BONE REMOVAL DEVICE

(75) Inventor: Alex Kunzler, LaQuinta, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 609 days.

(21) Appl. No.: 10/294,502

(22) Filed: Nov. 14, 2002

(65) Prior Publication Data

US 2003/0097134 A1 May 22, 2003

Related U.S. Application Data

(60) Provisional application No. 60/332,111, filed on Nov. 16, 2001.

(51) Int. Cl.
*A61B 10/00* (2006.01)
(52) U.S. Cl. .................. 606/79; 606/177; 606/171
(58) Field of Classification Search ............ 606/79, 606/80, 81, 171, 177, 178
See application file for complete search history.

(56) References Cited

U.S. PATENT DOCUMENTS

| | | | | |
|---|---|---|---|---|
| 3,978,862 A | * | 9/1976 | Morrison | 606/178 |
| 4,359,318 A | * | 11/1982 | Gittleman | 433/173 |
| 5,201,749 A | * | 4/1993 | Sachse et al. | 606/177 |
| 5,207,680 A | * | 5/1993 | Dietz et al. | 606/86 |
| 5,486,180 A | * | 1/1996 | Dietz et al. | 606/87 |
| 5,534,005 A | | 7/1996 | Tokish et al. | |
| 5,571,109 A | * | 11/1996 | Bertagnoli | 606/61 |
| 5,653,714 A | | 8/1997 | Dietz et al. | |
| 6,083,228 A | * | 7/2000 | Michelson | 606/79 |
| 6,159,214 A | * | 12/2000 | Michelson | 606/80 |
| 6,309,394 B1 | * | 10/2001 | Staehlin et al. | 606/79 |
| 6,436,101 B1 | * | 8/2002 | Hamada | 606/85 |
| 2004/0158254 A1 | | 8/2004 | Eisermann | |

OTHER PUBLICATIONS

U.S. Appl. No. 10/799,178, filed Mar. 12, 2004, Gil, et al.

* cited by examiner

*Primary Examiner*—Ralph A. Lewis
(74) *Attorney, Agent, or Firm*—Haynes and Boone, LLP

(57) ABSTRACT

An apparatus and method for positioning and controlling the movement of a bone removal device, and thus of controlling the profile of material removed by the device. Also an improved drive mechanism for a bone removal device, where the drive shaft is readily removable for maintenance or replacement, without significant disassembly of the device.

18 Claims, 15 Drawing Sheets

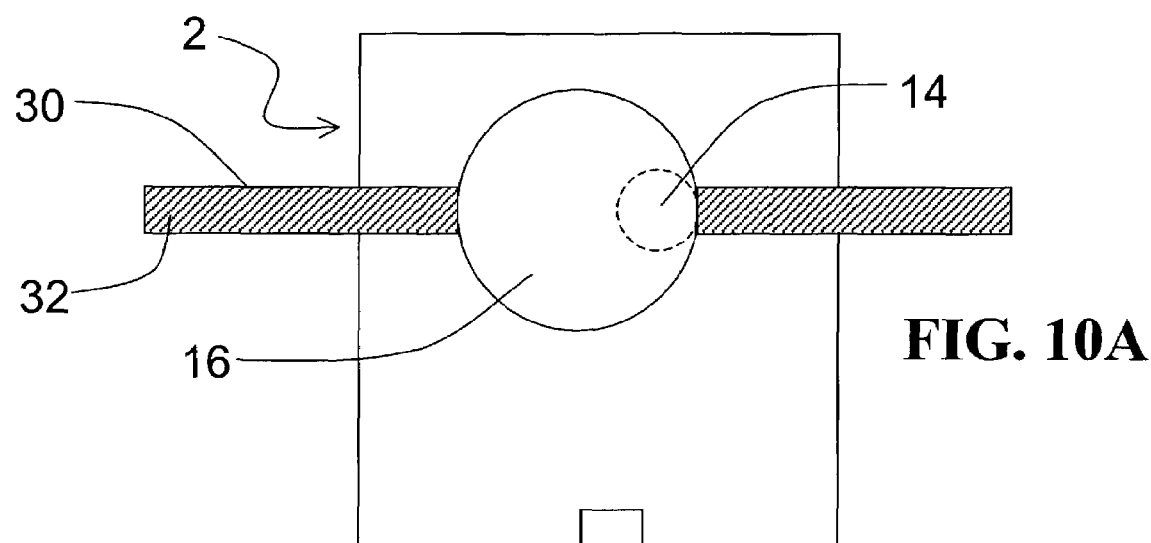
FIG. 10A
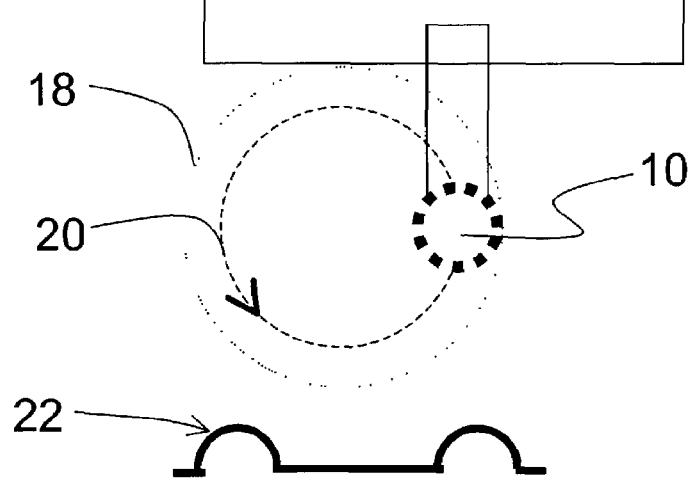
FIG. 10C
FIG. 10B

BONE REMOVAL DEVICE

This application claims the priority of U.S. Provisional Patent Application No. 60/332,111 filed Nov. 16, 2001, entitled "Bone Removal Device and Method of Use" incorporated herein by reference.

BACKGROUND

The invention relates to an apparatus and method for positioning and controlling the movement of a bone removal device, and thus of controlling the profile of material removed by the device. The invention also relates to an improved drive mechanism for a bone removal device, where the drive shaft is readily removable for maintenance or replacement, without significant disassembly of the device.

SUMMARY

The apparatus of the invention includes a support structure or cage adapted to receive a bone removal tool. Disposed in or on the support structure are one or more guide mechanisms that contain one or more portions capable of rotating with respect to the support structure, and that are adapted to be removably connected to the bone removal device. When the bone removal device is disposed in the support structure and connected to the guide mechanisms, the movement of the bone removal device with respect to the support structure is constrained and guided by the movement of the guide mechanism(s) within their range of rotation.

The invention relates to the support structure, its combination with one or more guiding mechanisms, and/or with a bone removal device whose range of motion is constrained with respect to the bone to be modified by the range of rotational motion of the guiding mechanism with respect to the support structure.

The invention also relates to a bone removal device having a removable drive shaft having a gearing arrangement allowing the shaft to be removed or replaced for maintenance and reinstalled without significant disassembly of the device.

BRIEF DESCRIPTION OF THE DRAWINGS

FIG. 10A is a schematic view of an alternative embodiment of the bone removal device of the present invention.

FIG. 10B is a profile of a bone removal element for use with the bone removal device of FIG. 10A.

FIG. 10C shows a bone removal profile created by the bone removal element of FIG. 10B utilized with the bone removal device of FIG. 10A.

DETAILED DESCRIPTION OF SPECIFIC EMBODIMENTS

The present invention relates to a unique bone removal device for preparing the end of a bone to receive a joint prosthesis. In particular, the device includes a bone removal tool movably mounted to a support structure or cage. The bone removal tool includes a housing having a proximal end and a distal end. A drive mechanism is contained within the housing. The internal design of the bone removal tool of the present invention may be the same as the designs described in copending U.S. patent application Ser. No. 09/934,507 filed on Aug. 22, 2001, entitled "Machining Apparatus," the entire contents of which are incorporated herein by reference.

A bone removal element is mounted at the distal end of the housing. The proximal end of the housing is adapted to be attached to a drive source to drive the drive mechanism.

A guide mechanism that interconnects the bone removal tool and the support structure is positioned between the proximal end and the distal end of the housing. The guide mechanism is designed to allow the user to guide the movement of the device, and in particular to guide the movement of the bone removal element in order to create a specific shape or profile within or in the end of the bone.

In accordance with one embodiment, the guide mechanism consists of one or more offset shafts. Each shaft has a first guide pin and a second guide pin associated therewith. The first guide pin is rotatably attached to the support structure. The second guide pin is rotatably mounted on the bone removal tool. In use, the bone removal tool is manipulated by the user such that the first guide pin and the second guide pin rotate about one another, and thereby guide the motion of the bone removal element along a predetermined path.

Figure 1:
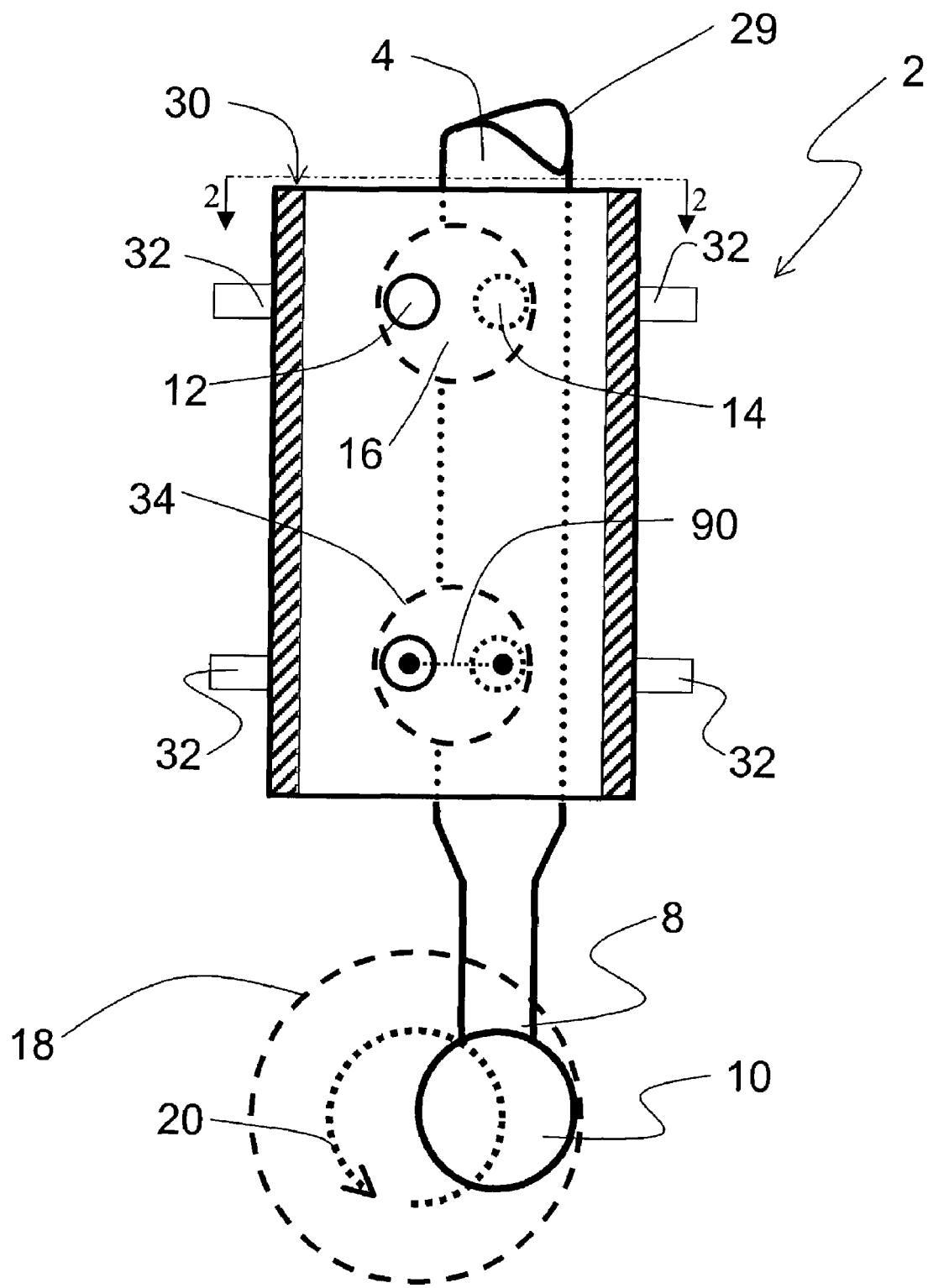
FIG. 1 is a partial cross sectional schematic plan view of a bone removal device in accordance with the present invention.
Figure 2:
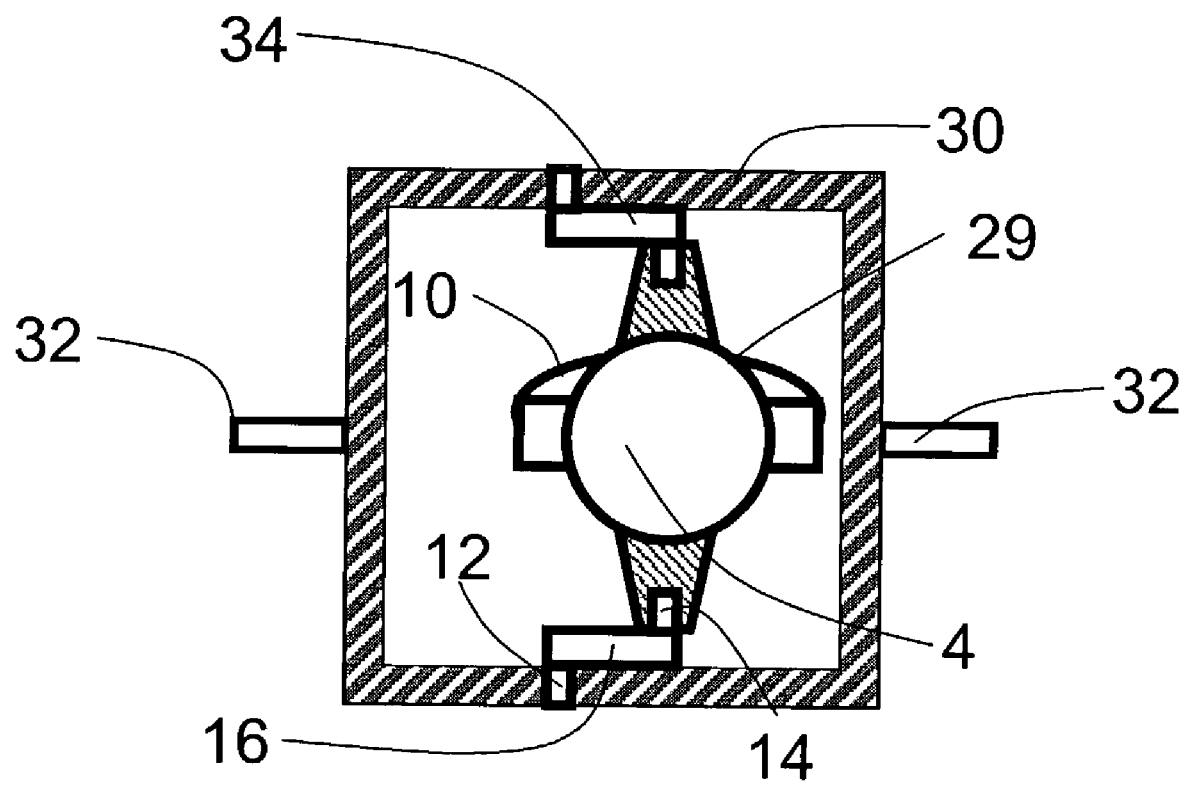
FIG. 2 is a top view of the bone removal device of FIG. 1 taken along the line 2-2.

Referring now to the drawings, various embodiments of the present invention are illustrated. Referring to FIGS. 1 and 2, bone removal device 2 is shown. The device 2 includes a bone removal tool 29 and a cage (or guide body) 30. Bone removal tool 29 includes housing 4 having a proximal end (not shown) and a distal end 8. A bone removal element 10 is positioned at the distal end 8 of the housing 4. Bone removal element 10 may incorporate a variety of mechanisms to remove bone. For example, bone removal element 10 may include a mechanical mechanism to remove bone such as a cutting edge, an abrasive surface, or a combination thereof. Alternatively, bone removal element may include a tissue obliteration mechanism such as an electron or RF beam, ultrasound, or fluid jet cutting.

Cage 30 includes at least one set of pivot pins 32. The pivot pins 32 are adapted to interface with a machining jig or scaffold (not shown) similar to the scaffold designs described in co-pending U.S. patent application Ser. No. 09/923,891 filed on Aug. 7, 2001 entitled "Method and Apparatus for Stereotactic Implantation," the entire contents of which is incorporated herein by reference.

Figure 3:
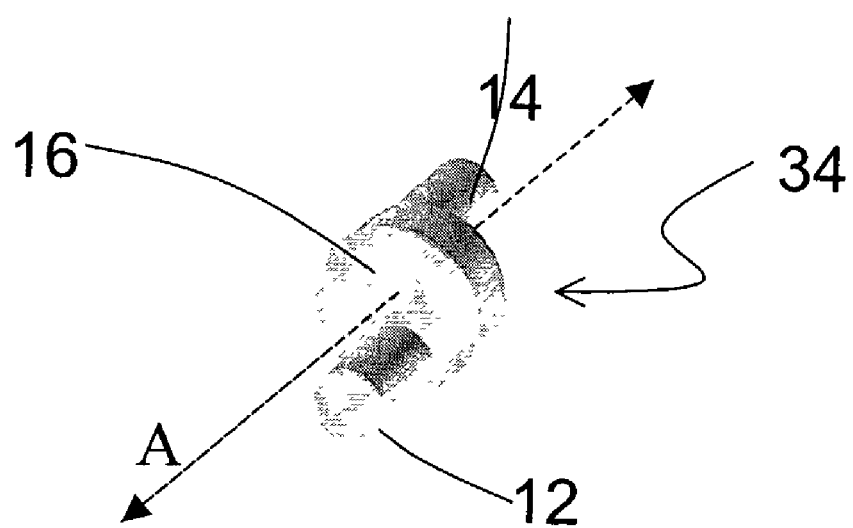
FIG. 3 is a perspective view of a guide mechanism utilized in the bone removal device illustrated in FIG. 1.

Cage 30 is movably attached to bone removal tool 29 via a guide mechanism (or guide member) 34. In accordance with one embodiment, guide mechanism 34 includes an offset shaft. As seen best in FIG. 3, offset shaft 34 includes first and second guide pins 12, 14 interconnected by body 16. The axis of the first and second guide pins 12, 14 are substantially parallel, but are not congruent to one another. As best illustrated in FIG. 2, first guide pin 12 is rotatably attached to cage 30. Second guide pin 14 is rotatably attached to housing 4. Alternatively, guide pins 12, 14 could be rotatably attached to body 16, and non-movably attached to cage 30 and/or housing 4. In use, housing 4 is moved such that guide pin 14 causes body 16 to rotate about its axis A (see FIG. 3). As body 16 rotates, bone removal element rotates along arrow 20 to create a first bone removal profile 18 (see FIG. 1) within a first plane.

Figure 4:
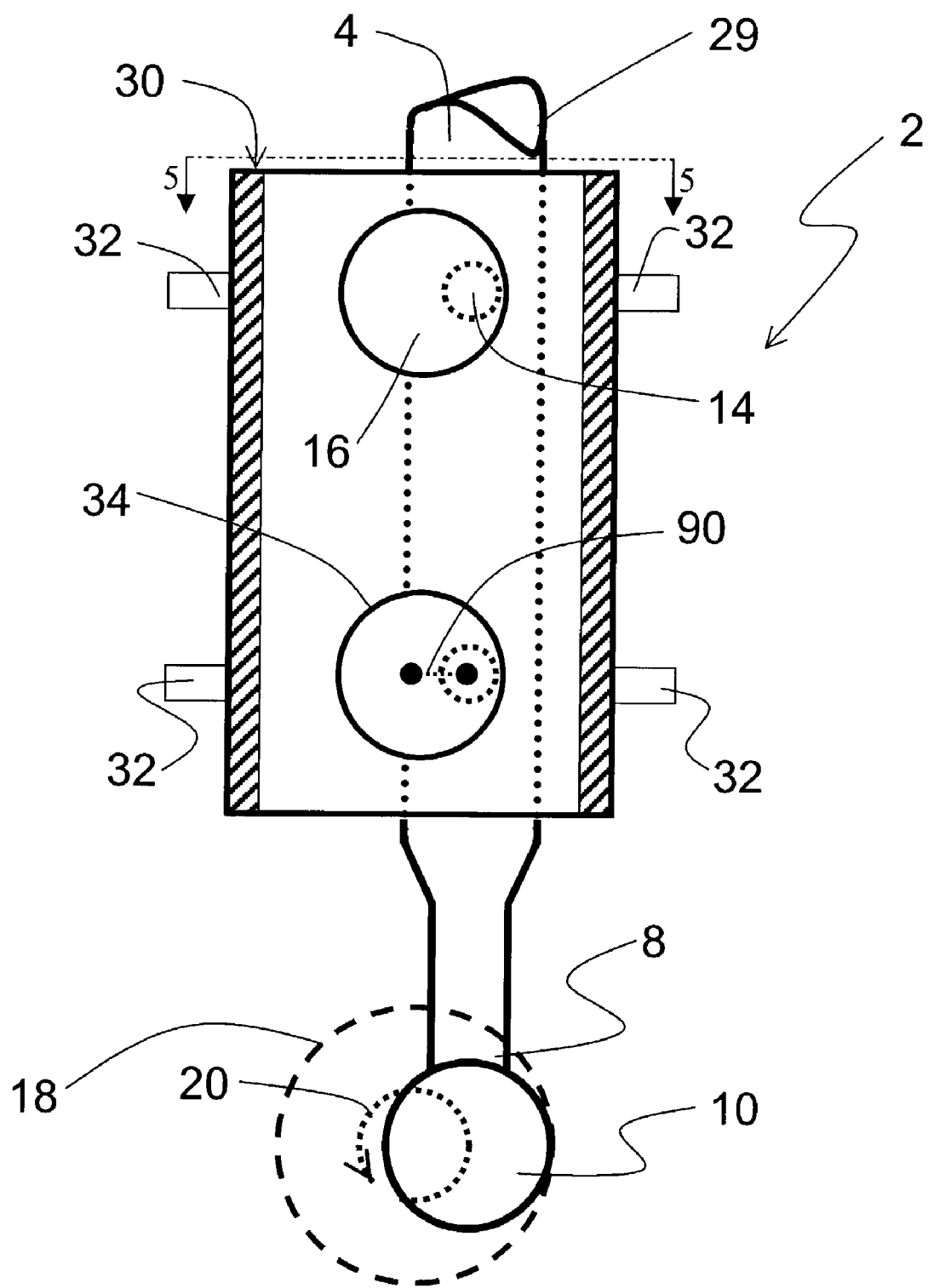
FIG. 4 is a partial cross sectional schematic plan view of an alternative embodiment of a bone removal device in accordance with the present invention.
Figure 5:
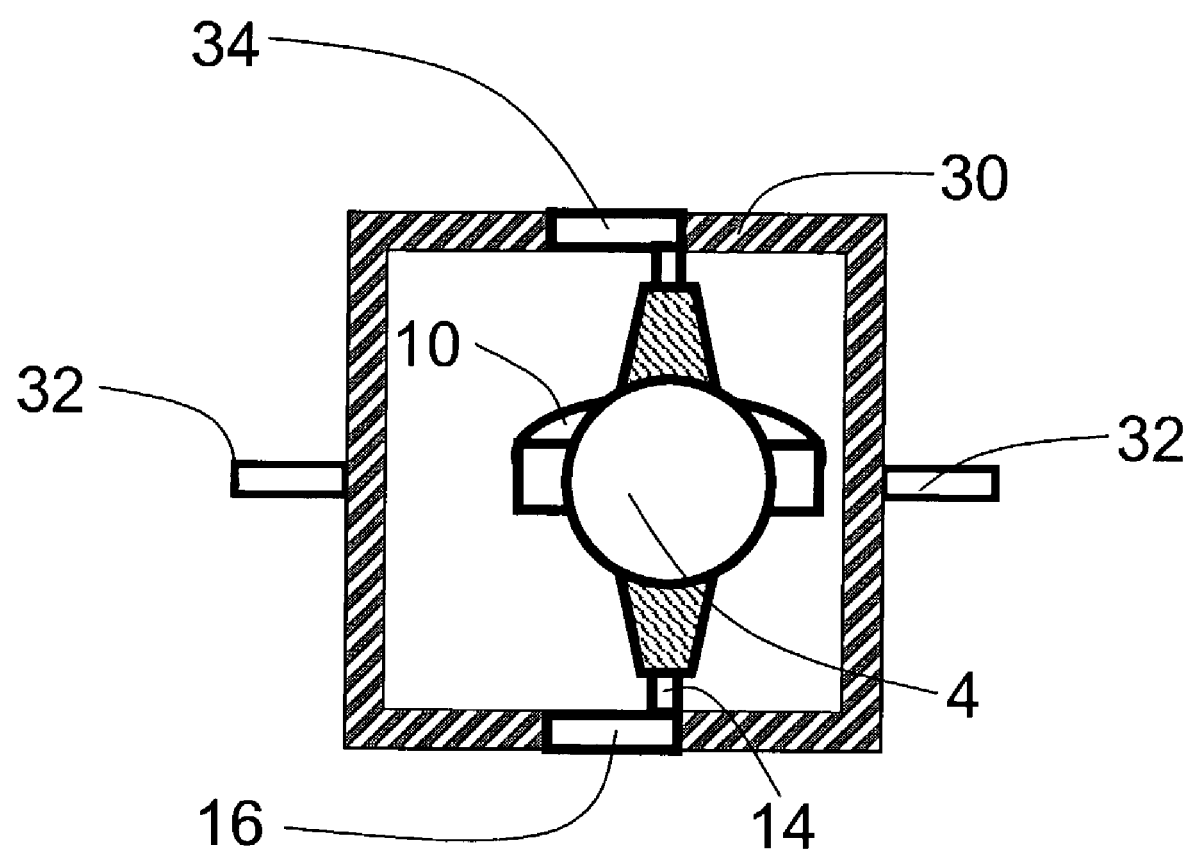
FIG. 5 is a top view of the bone removal device of FIG. 4 taken along the line 5-5.
Figure 6:
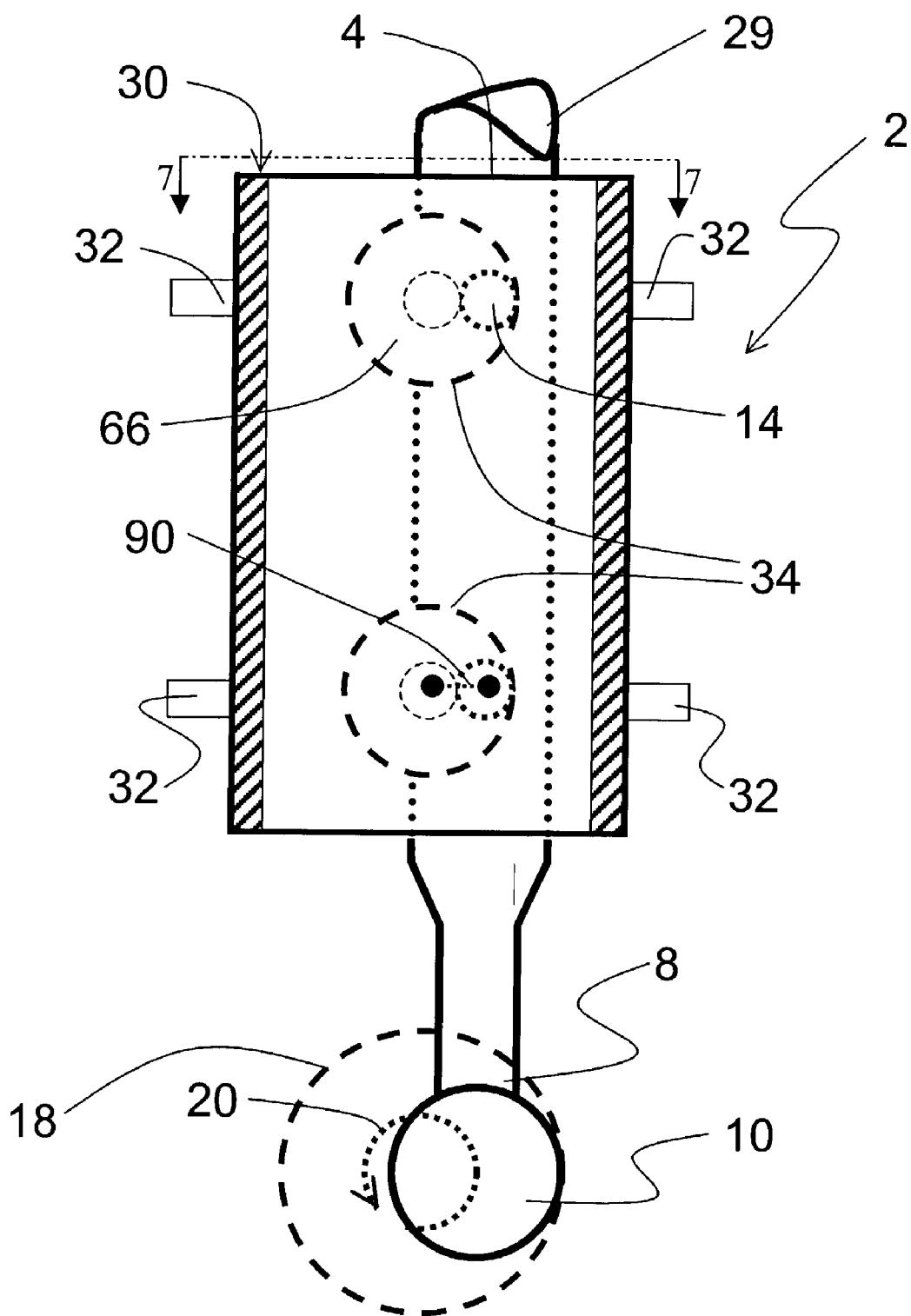
FIG. 6 is a partial cross sectional schematic plan view of yet another alternative embodiment of a bone removal device in accordance with the present invention.
Figure 7:
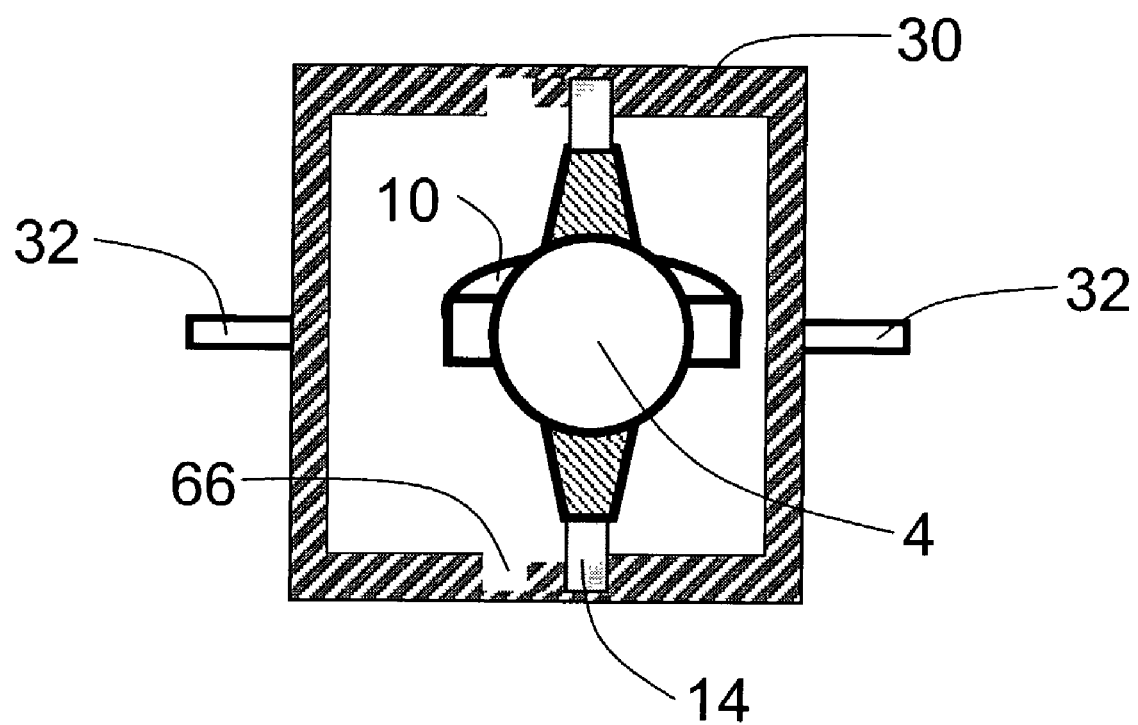
FIG. 7 is a top view of the bone removal device of FIG. 6 taken along the line 7-7.

FIGS. 4 and 5 illustrate an alternative embodiment of guide mechanism 34. In accordance with this embodiment, guide mechanism 34 consists of a body 16 rotatably positioned within an opening in cage 30 and a pin 14 rotatably attached to housing 4. As with the previous embodiment, as body 16 rotates, bone removal element rotates along arrow 20 to create a first bone removal profile 18 within a first plane FIGS. 6 and 7 illustrate yet another embodiment of guide mechanism 34. In accordance with this embodiment, the guide mechanism consists of a track 66 within the side of cage 30. Guide pin 14 is positioned within track 66. Housing 4 may be moved such that pins 14 rotate about tracks 66 thereby causing bone removal element to rotate along arrow 20 to create first bone removal profile 18 within a first plane.

Figure 9A:
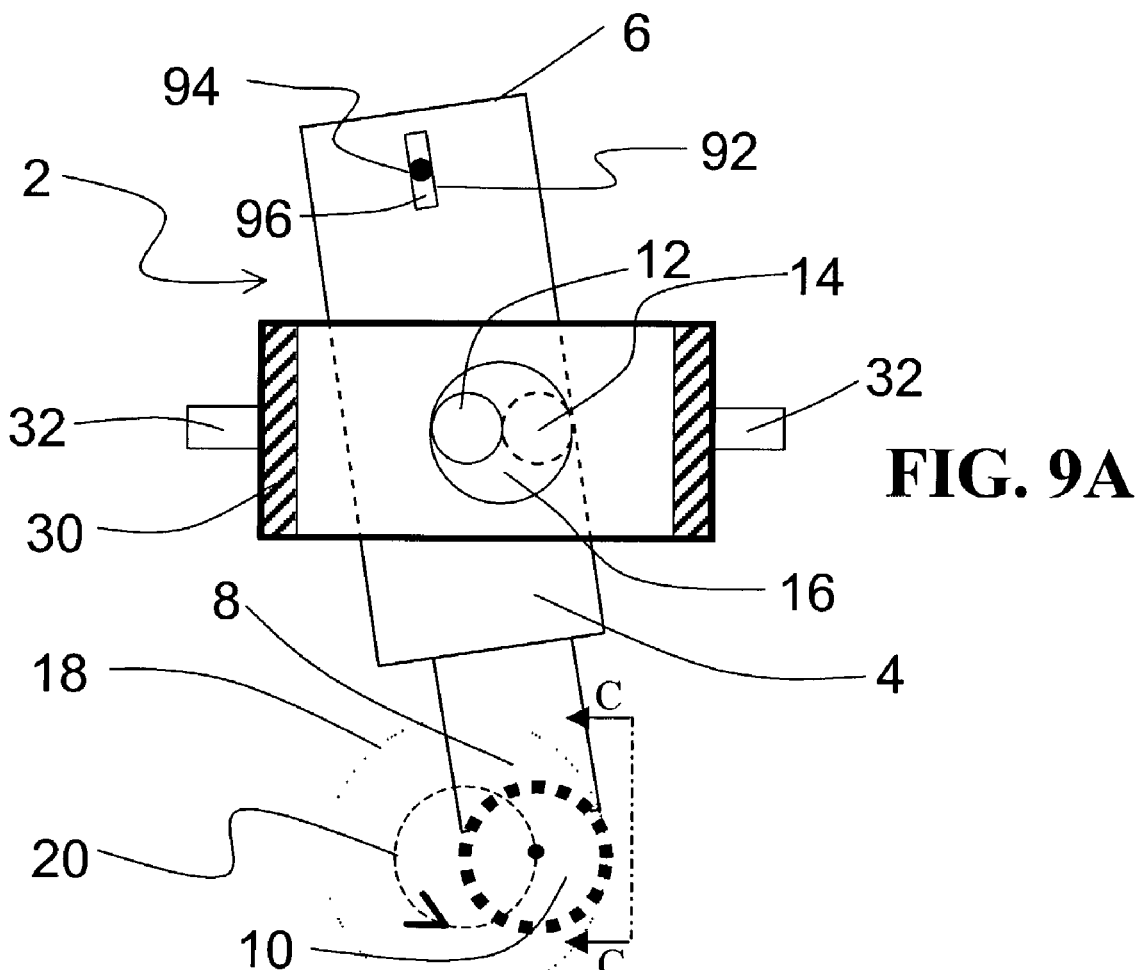
FIG. 9A is a schematic view of an alternative embodiment of the bone removal device of the present invention.
Figure 9C:
FIG. 9C shows a bone removal profile created by the bone removal element of FIG. 9B utilized with the bone removal device of FIG. 9A.
Figure 9B:
FIG. 9B is a profile of a bone removal element for use with the bone removal device of FIG. 9A.
Figure 11A:
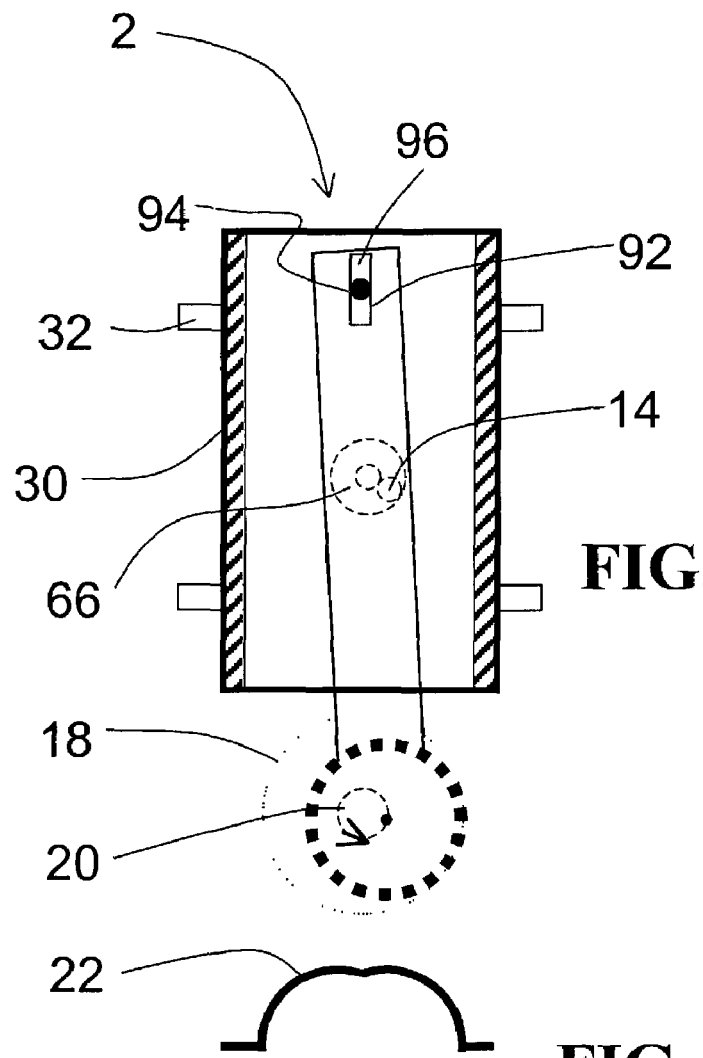
FIG. 11A is a schematic view of an alternative embodiment of the bone removal device of the present invention.
Figure 11C:
FIG. 11C shows a bone removal profile created by the bone removal element of FIG. 11B utilized with the bone removal device of FIG. 11A.
Figure 11B:
FIG. 11B is a profile of a bone removal element for use with the bone removal device of FIG. 11A.
Figure 12A:
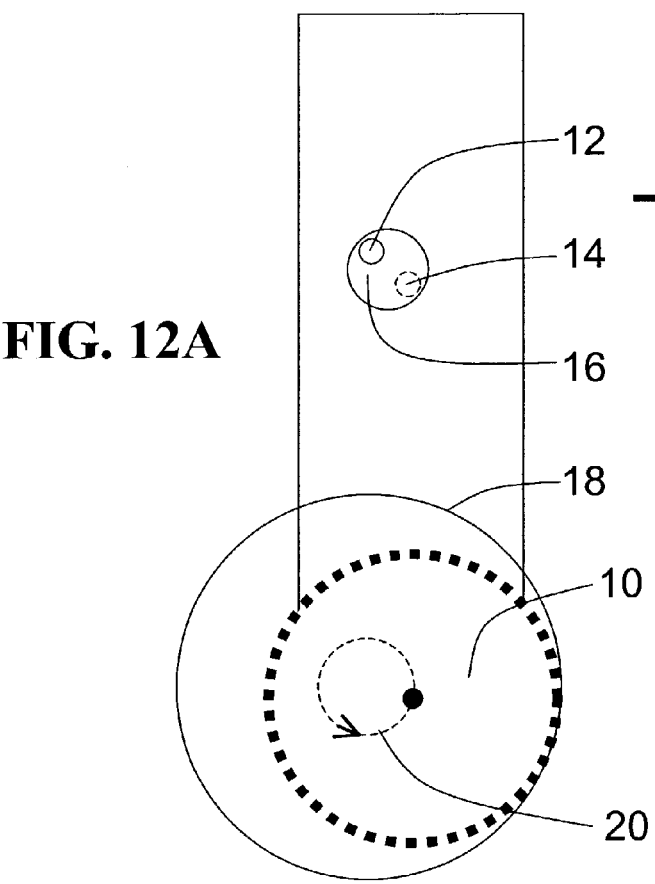
FIG. 12A is a schematic view of an alternative embodiment of the bone removal device of the present invention.
Figure 12C:
FIG. 12C shows a bone removal profile created by the bone removal element of FIG. 12B utilized with the bone removal device of FIG. 12A.
Figure 12B:
FIG. 12B is a profile of a bone removal element for use with the bone removal device of FIG. 12A.
Figure 13A:
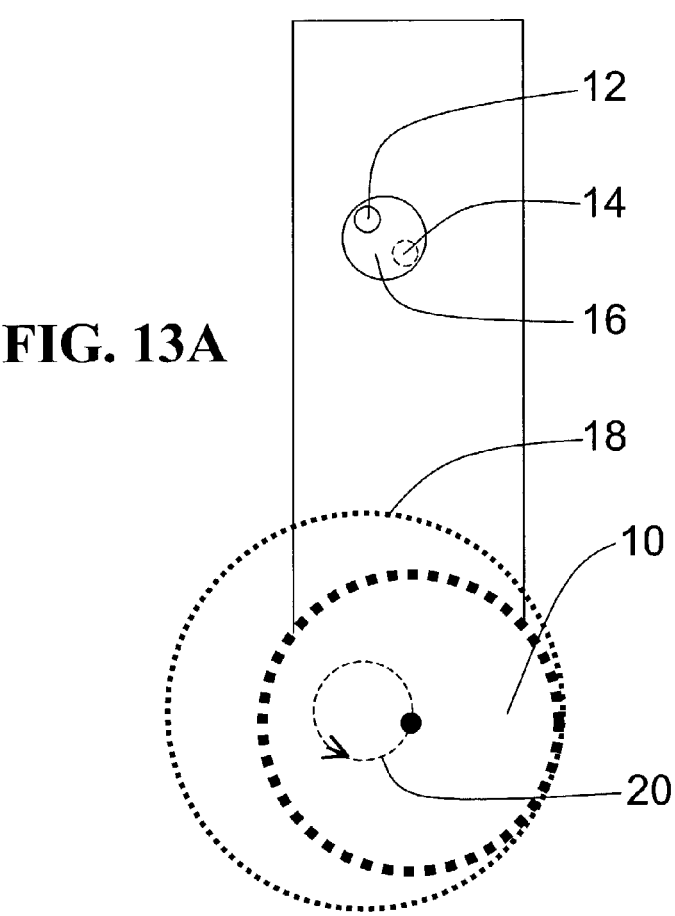
FIG. 13A is a schematic view of an alternative embodiment of the bone removal device of the present invention.
Figure 13C:
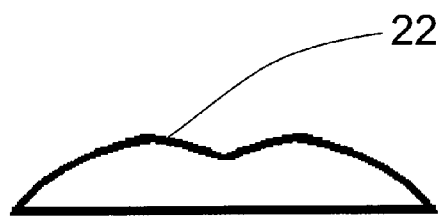
FIG. 13C shows a bone removal profile created by the bone removal element of FIG. 13B utilized with the bone removal device of FIG. 13A.
Figure 13B:
FIG. 13B is a profile of a bone removal element for use with the bone removal device of FIG. 13A.

In the embodiments shown in FIGS. 1-7, guide mechanism 34 is shaped to create a circular bone removal profile 18. Those skilled in the art will appreciate that the shape of guide mechanism 34 can be modified to create a bone removal profile 18 having any one of a variety of shapes. For circular bone removal profiles 18, the radius of the profile is determined by the radius of the bone removal element 10 and the radius of the path 20 of the center of the bone removal element. The radius of path 20 is determined by the critical radius dimension 90 of the guide mechanism 34 as illustrated in FIG. 1, FIG. 4 and FIG. 6. In addition, each of the embodiments illustrated in the drawings includes two guide mechanisms on two sides of device 2. Alternatively, the device could include only one guide mechanism on one side of device 2, one guide mechanism on two sides of device 2, two guide mechanisms on one side of device 2, or a plurality of guide mechanisms on one or more sides of device 2. As illustrated in FIGS. 9-11, in those embodiments where only one guide mechanism 34 is included on one side of a device 2, a stabilizing structure 92 may be provided to facilitate guiding bone removal element 10 along profile 18. Stabilizing structure 92 may include a pin 94 attached to housing 4 positioned within a slot 96 within support structure 30.

Figure 8A:
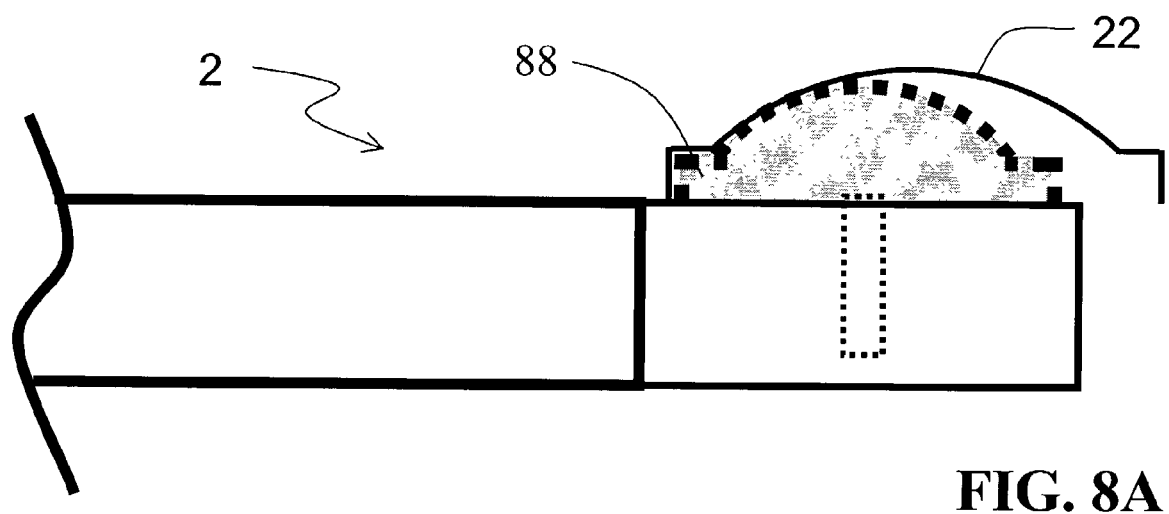
FIG. 8A is a side view of the distal end of the bone removal device shown in FIG. 1.
Figure 8B:
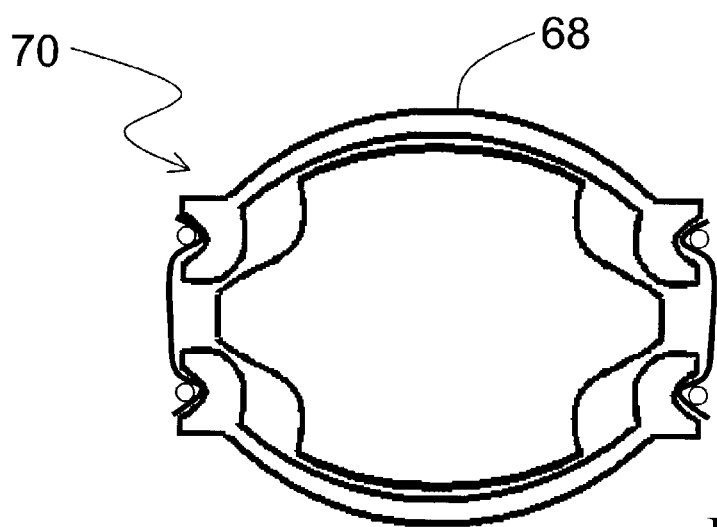
FIG. 8B is a side view of a prosthesis that may be implanted into an opening prepared using the bone removal device of FIG. 8A.

FIG. 8A is a schematic view of the distal end of device 2 shown in FIG. 1, and illustrates a second bone removal profile 22 within a second plane that is substantially perpendicular to the first plane in which bone removal profile 18 lies. The bone removal device creates the second bone removal profile 22 as body 16 of guide mechanism 34 rotates about its axis. FIG. 8B illustrates the exterior profile 68 of a joint prosthesis 70. In accordance with the present invention, the exterior profile 68 of joint prosthesis 70 substantially matches the second bone removal profile 22. Similarly, although not illustrated in the drawings, the profile of the prosthesis along the first plane substantially matches the first bone removal profile 18.

FIGS. 9A-13C illustrate alternative embodiments of the present invention. In each of these Figures. FIGS. 9A, 10A, 11A, 12A, and 13A represent a schematic drawing of a bone removal device 2 in accordance with the present invention. FIGS. 9B, 10B, 11B, 12B, and 13B represents the lateral profile of the bone removal element 10 shown in the corresponding figure A. FIGS. 9C, 10C, 11C, 12C, and 13C represent the second bone removal profile 22 created by the device shown in the corresponding figure A when used with the bone removal device 2 of the corresponding figure B. For ease of illustration the support structure or cage is not shown in all embodiments. One skilled in the art will appreciate from these figures that the device of the present invention may create a variety of profiles within a bone surface. The exact profile will be determined by: 1) the size and shape of the guiding mechanism; and the size and shape of the bone removal element within both the first and the second planes. As noted above, although the guide mechanism is illustrated as being essentially circular, it (as well as the shape of the bone removal element along the first and second planes) may also be elliptical, square, hexagonal, or any other polygonal shape, or may include shapes that are only partially arcuate or formed from a plurality of arcs with different radii of curvature. Preferably, the bone removal element has a profile along the second plane that consists of two merged profiles that are mirror images of one another. An example of such a profile is shown in FIG. 13B. In this embodiment the bone removal element has a non-circular profile that consists of two merged mirrored arcs, whereby each arc has the same radius of curvature. The bone removal element profile may also include a shoulder 88 as shown in the device illustrated in FIG. 8A. One skilled in the art will further appreciate that a prosthesis may be provided having an outer surface that substantially matches or complements the profile created by the bone removal device 2.

Figure 14A:
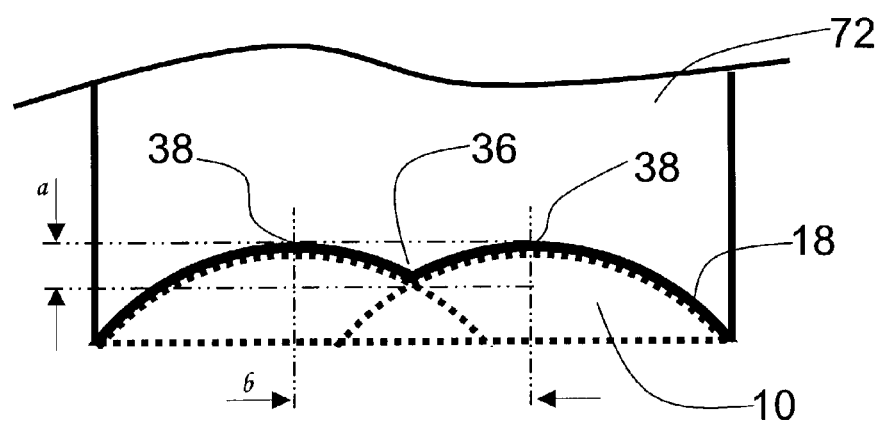
FIG. 14A is a schematic drawing of a bone removal profile created by an embodiment of a bone removal device of the present invention.
Figure 14B:
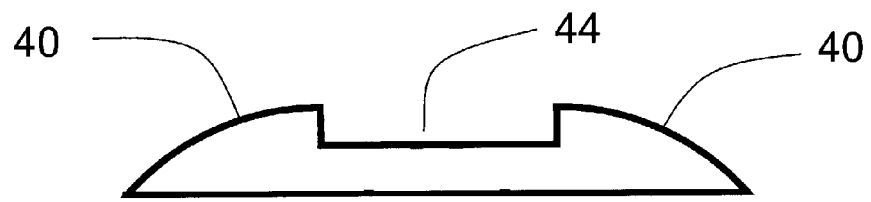
FIG. 14B is a schematic drawing of the complementary profile of a portion of the prosthesis implanted within that bone removal profile in accordance with a method of the present invention.

FIGS. 14A and 14B illustrate an outer surface of a possible prostheses design and its complementary bone removal profile. As shown in FIG. 14A, bone removal element 10 (whose positions are illustrated by the dotted lines) rotates as described above to create a bone removal profile 18 within a bone 72. In accordance with this embodiment, a central protruding bone portion 36 is created by the bone removal element 10. The protruding portion 36 extends between the two apexes 38 of the bone removal profile 18, and has a width of $\delta$ and a height of $\alpha$. As shown in FIG. 14B, the complimentary prosthesis surface profile includes an outer radial section 40 and a central recessed section 44 designed to accommodate the bone protrusion 36. In particular, recessed section 44 has a width that is greater than $\delta$ and a height that is greater than $\alpha$. Outer radial section 40 has substantially the same radius of curvature as a portion of the bone remove element 10 and the bone removal profile 18 created thereby.

Figure 15:
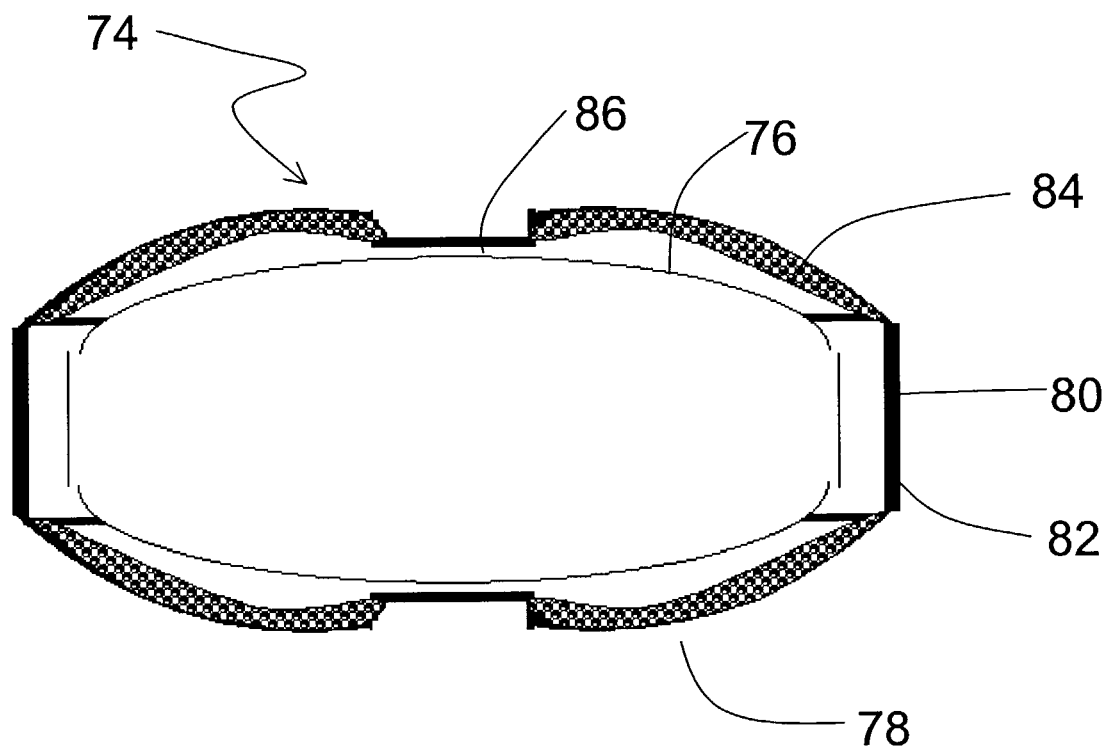
FIG. 15 is a cross sectional view of a prosthesis that may be implanted into an opening prepared using the bone removal device of the present invention.

FIG. 15 is a cross sectional view of a spinal disc prosthesis 74 that may be implanted in accordance with the present invention. Prosthesis 74 is similar in design to the devices described in co-pending U.S. patent application Ser. No. 09/924,298 filed on Aug. 8, 2001 entitled "Implantable Joint Prosthesis," and which is incorporated herein by reference. Prosthesis 74 includes an upper shell 76, a lower shell 78 and a central component 80 positioned between the two shells. The prosthesis 74 further includes an annular sheath 82 that is attached to the upper and lower shells 76, 78 and surrounds the central component 80. Sheath 82 seals the central component from the external environment. A portion of the outer surface of the shells 76, 78 includes a bone ingrowth surface 84. Preferably, the bone ingrowth surface 84 is a porous coating. As shown in FIG. 15, each of the shells 76, 78 of prosthesis 74 includes a central recessed portion 86 defined by the absence of the porous coating. In accordance with the present invention, a bone removal device having a bone removal element profile similar to that shown in FIG. 14A is provided to prepare a vertebral endplate to receive prosthesis 74. In accordance with this embodiment of the present invention, the bone removal element profile is sized and shaped such that a protrusion 36 having a height and width that is smaller than the height and width of the recessed portion 86 of prosthesis 74.

Figure 16:
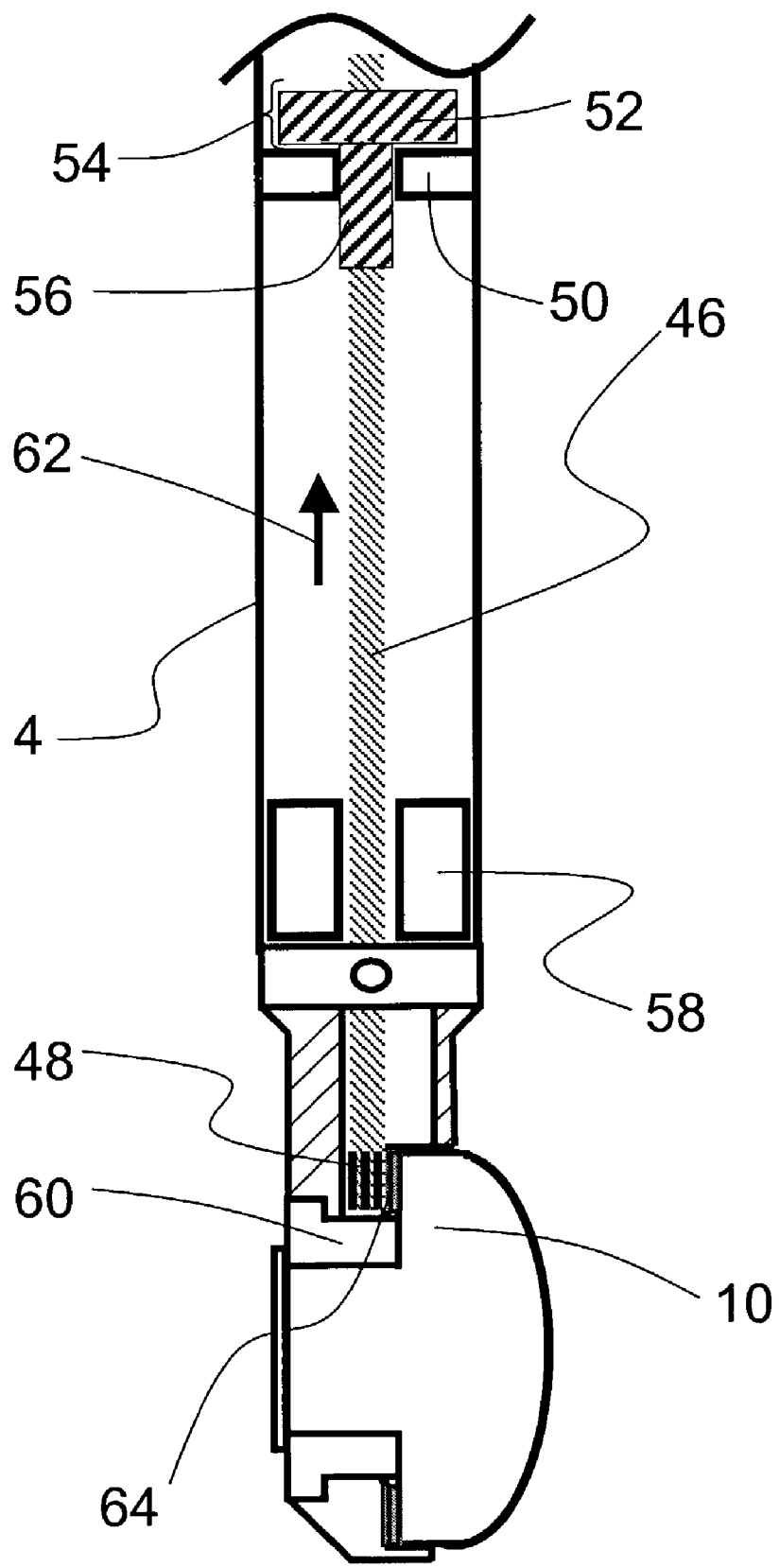
FIG. 16 is a cross sectional schematic view of a bone removal device in accordance with the present invention, and in particular, illustrates a unique drive mechanism.

FIG. 16 is a schematic cross sectional view of a bone removal device in accordance with the present invention, and illustrates a unique drive mechanism. The drive mechanism includes a drive shaft 46 having gears 48 located at its distal end that are adapted to interface with gears 64 located on the under surface of bone removal element 10. The proximal end (not shown) of drive shaft 46 is adapted to be attached to a standard power source such as, for example, by means of any well-known mechanical interlocking coupling. The housing 4 of the device includes a proximal support member 50 through which drive shaft 46 extends. Drive shaft 46 includes a rotation-facilitating segment 52 having an expanded section 54 and a support member interface section 56. In accordance with a preferred embodiment of the present invention, drive shaft 46 is made from a biocompatible material such as, for example, a biocompatible metal or a biocompatible polymer. Preferably, drive shaft 46 is made from stainless steel. Rotation facilitating segment 52 is preferably made from a wear resistant ceramic or polymer, such as a Teflon impregnated Delrin. In addition, the support members 50 are desirably made from stainless steel. To further facilitate rotation of shaft 46 a bushing 58, which may be made of ceramic or other suitable bushing material, is mounted along the shaft within housing 4. In addition, bone removal element 10 is mounted on a similar bushing 60 to facilitate its movement. In use, this design provides a disposable drive shaft 46 that can be quickly and easily removed and replaced when the gears 48 become worn. Shaft 46 is removed from housing 4 by pulling its proximal end in the direction of arrow 62. When a new shaft 46 is inserted, expanded section 54 provides a stop mechanism against support members 50 to properly position shaft 46 along the longitudinal axis of the device. When a motor or drive mechanism is coupled to the proximal end of the device it locks shaft 46 in place. Although the gearing arrangement is illustrated as a spur gear-type pinion on shaft 46 and a face gear on one surface of the bone removal element 10, other gearing arrangements are possible, so long as the gear on shaft 46 is removable through the apertures in housing 4, and is easily inserted and coupled with the other gears in the arrangement. Possible examples include bevel gears, or a face gear on the end of shaft 46 that couples with gearing around the edge of bone removal element 10.

The foregoing description of specific embodiments is illustrative of the invention claimed below and without limitation to its understanding and practice, it being understood that alternative of the specific embodiments herein utilizing the disclosed concepts are intended to be within the full scope of the claimed invention.

I claim:

1. A bone preparation device, comprising:
   a guide body;
   a bone removal device having a longitudinal axis extending between a proximal portion and a distal portion; and
   a guide member movably engaged between said guide body and said bone removal device, wherein said bone removal device may be rotatably guided about at least two axes of said guide member through a predetermined pattern, wherein said guide body is a cage at least partially encircling said bone removal device, wherein said body has an inner surface, said inner surface having a track, said guide member following said track to control said bone removal device to form said predetermined pattern.

2. The apparatus of claim 1, wherein said guide member is rotatably connected to said bone removal device.

3. The apparatus of claim 1, wherein said guide member is rotatably connected to said guide body.

4. The apparatus of claim 1, wherein said predetermined pattern is circular.

5. The apparatus of claim 4, wherein said bone removal device forms a generally toroidal shape in the bone.

6. The apparatus of claim 1, wherein said guide member has a major side surface substantially parallel to said longitudinal axis and said guide body is joined to said major side surface.

7. The apparatus of claim 6, wherein said predetermined pattern is defined in a plane substantially parallel to said longitudinal axis.

8. The apparatus of claim 1, wherein said guide member includes a first projection pivotally engaged to said bone removal device.

9. The apparatus of claim 8, wherein said guide member includes a second projection in substantial opposition to said first projection, said second projection pivotally engaged with said guide body.

10. The apparatus of claim 1, wherein said bone removal device includes a bone removal element disposed adjacent said distal end, said bone removal element having an axis of rotation, said axis of rotation offset with respect to said longitudinal axis.

11. The apparatus of claim 10, wherein said axis of rotation is substantially transverse to said longitudinal axis.

12. The apparatus of claim 1, wherein said bone removal device is coupled to a power source adjacent said proximal end.

13. The apparatus of claim 1, wherein said guide member is configured to simultaneously control axial displacement of said bone removal device with respect to said guide body and movement transverse to said longitudinal axis to generate a substantially non-linear predetermined pattern.

14. The apparatus of claim 1, wherein said guide member is pivotally connected to said bone removal device.

15. A bone preparation device, comprising:
a guide body having a central axis along said guide body;
a bone removal device having a longitudinal axis extending between a proximal portion and a distal portion; and
a guide member movably engaged between said guide body and said bone removal device, wherein said bone removal device may be rotatably guided about at least two axes of said guide member through a predetermined pattern, wherein one of the axes is rotatably guided about the other of the axes such that said longitudinal axes of said bone removal device remains substantially parallel to the central axes of said guide body, wherein said guide body is a cage at least partially encircling said bone removal device, wherein said body has an inner surface, said inner surface having a track, said guide member following said track to control said bone removal device to form said predetermined pattern.

16. The apparatus of claim 15, wherein said guide member is pivotally connected to said bone removal device.

17. A kit, comprising:
an implant having an outer surface for substantial engagement with a bone surface, said outer surface having an indentation;
a guide body;
a bone removal device having a longitudinal axis extending between a proximal portion and a distal portion; and
a guide member movably engaged between said guide body and said bone removal device, wherein said bone removal device may be rotated by said guide member with respect to said guide body through a predetermined pattern to define a projection in a bone surface substantially corresponding to said indentation, wherein said implant is an artificial disc and said projection is defined in at least one endplate of a vertebral body.

18. A bone preparation device, comprising:
a guide body;
a bone removal device having a longitudinal axis extending between a proximal portion and a distal portion; and
a guide member movably engaged between said guide body and said bone removal device, wherein said bone removal device may be rotatably guided about at least two axes of said guide member through a predetermined pattern, wherein one of the axes is rotatably guided about the other of the axes, wherein said guide body is a cage at least partially encircling said bone removal device, wherein said guide body has an inner surface, said inner surface having a track, said guide member following said track to control said bone removal device to form said predetermined pattern.

* * * * *